United States Patent [19]

Mowrey-McKee et al.

[11] Patent Number: 5,756,044
[45] Date of Patent: May 26, 1998

[54] APPARATUS AND METHOD FOR TREATING ARTICLES IN SOLUTION WITH EFFERVESCENT TABLETS

[75] Inventors: Mary Mowrey-McKee, Alpharetta; Rafael Victor Andino, Lawrenceville; David N. Ku, Atlanta, all of Ga.; Paul J. Mulhauser, New York, N.Y.; David R. Schiff, Highland Park, N.J.

[73] Assignee: CIBA Vision Corporation, Duluth, Ga.

[21] Appl. No.: 629,715

[22] Filed: Apr. 9, 1996

[51] Int. Cl.⁶ .................................................. A61L 2/00
[52] U.S. Cl. ........................ 422/28; 422/300; 422/301; 422/310
[58] Field of Search ....................... 134/901, 137, 134/143; 422/301, 102, 300, 310, 28; 220/608, 633, 635; 215/1 C

[56] References Cited

U.S. PATENT DOCUMENTS

| | | | |
|---|---|---|---|
| 4,011,941 | 3/1977 | Parsons | 206/5.1 |
| 4,473,550 | 9/1984 | Rosenbaum et al. | 424/94 |
| 4,485,963 | 12/1984 | Panicci | 229/7 S |
| 4,588,586 | 5/1986 | Kessler et al. | 435/78 |
| 4,637,919 | 1/1987 | Ryder et al. | 422/300 |
| 4,750,610 | 6/1988 | Ryder | 206/5.1 |
| 4,956,156 | 9/1990 | Kanner et al. | 422/300 |
| 4,996,027 | 2/1991 | Kanner | 422/113 |
| 5,164,166 | 11/1992 | Stepanski et al. | 422/297 |
| 5,169,455 | 12/1992 | Kessler | 134/42 |
| 5,186,317 | 2/1993 | Ryder et al. | 206/5.1 |
| 5,250,266 | 10/1993 | Kanner | 422/113 |
| 5,292,488 | 3/1994 | Cerola et al. | 422/292 |
| 5,328,846 | 7/1994 | Wedler | 435/264 |
| 5,384,091 | 1/1995 | Rontome et al. | 422/30 |
| 5,491,091 | 2/1996 | Loshaek et al. | 436/1 |

FOREIGN PATENT DOCUMENTS

| | | |
|---|---|---|
| 0411887 | 7/1990 | European Pat. Off. |
| 0476937A | 9/1991 | European Pat. Off. |
| WO9409399 | 4/1994 | WIPO |

OTHER PUBLICATIONS

European Search Report.

*Primary Examiner*—Laurie Scheiner
*Assistant Examiner*—Jeffrey Stucker
*Attorney, Agent, or Firm*—R. Scott Meece; Michael U. Lee

[57] ABSTRACT

An article treatment system which provides improved solution mixing and concentration uniformity. The treatment system includes a container, a closure and a channel for guiding fluid flow. The treatment system is especially advantageous for use with effervescent tablets and for use in treating contact lenses. Cleaning and disinfecting of articles is improved by use of a tubular channel which guides upwardly gas and other components released from an effervescent tablet which is located at the bottom of the treatment container. The upward central flow through the channel induces a downward flow between the container walls, the exterior walls of the channel, and the article-retaining means and towards the bottom of the container.

28 Claims, 5 Drawing Sheets

APPARATUS AND METHOD FOR TREATING ARTICLES IN SOLUTION WITH EFFERVESCENT TABLETS

BACKGROUND OF THE INVENTION

1. Field of the Invention

This invention relates broadly to containers useful in facilitating mixing of solutions retained therein by application of gas bubbles. More specifically, this invention relates to contact lens care containers for use with effervescent tablets. In a preferred embodiment, this invention relates to containers for cleaning and disinfecting ophthalmic lenses.

2. Description of the Related Art

Contact lenses should be disinfected when removed in order to eradicate harmful microorganisms which may cause ocular diseases. It is common for consumers to remove lenses overnight and disinfect lenses daily. In addition, contact lenses should be cleaned periodically in order to remove lipid and protein deposits which impair vision. Ideally, the consumer would prefer to clean and disinfect contact lenses in a "one-step" process. Numerous compositions, methods and devices for disinfecting, cleaning and simultaneously cleaning and disinfecting contact lenses have been disclosed. Examples of patents and publications relating to cleaning and disinfecting follow.

U.S. Pat. No. 4,473,550, issued to Rosenbaum, et al. on Sep. 25, 1984, describes a method for disinfecting a contact lens with a three component solution. The solution includes a peroxide, a peroxidase within the classification E.C. 1.11–1.7 and donor molecules adapted to act as a substrate for said peroxidase, with each of the three components being in a dry state such that the bactericide is inactive; admixing the three components in a liquid carrier solution to cause a catalyzed reaction by said peroxidase for generating free radicals from said source of donor molecules, immersing the contact lens into said solution substantially simultaneous with the admixture of all three components whereby bacteria present on said contact lens will be killed during said limited period of bacteriological activity.

U.S. Pat. No. 4,588,586, issued to Kessler, et al. on May 13, 1986, describes a method of forming a bactericide comprising a peroxide, a peroxidase and a source of donor molecules adapted to act as a substrate for the peroxidase. The method involves storing the three components in a non-reacting state, then mixing in a liquid carrier for contact lens immersion therein.

U.S. Pat. No. 5,169,455, issued to Kessler on Dec. 8, 1992, discloses a method of simultaneously cleaning and disinfecting contact lenses with a proteolytic enzyme and a peroxidative reaction with donor and acceptor molecules. The composition disclosed uses a thiol agent as a color indicator. A preferred composition includes peroxidase, iodide, hydrogen peroxide, a protease and a thiol agent. Useful proteases disclosed include trypsin, collaginases, keratinase, elastase, aminopeptidases, carboxylases, pancreatin, pronases and subtilisin.

U.S. Pat. No. 5,186,317, issued to Ryder, et al. on Feb. 16, 1993, discloses a lens case for contact lens disinfection systems which use disinfecting tablets or catalysts. The system includes a cylindrical cup which has a reaction chamber in the bottom for holding a tablet. The reaction chamber has substantially reduced dimensions with respect to the cylindrical main body portion of the cup.

U.S. Pat. No. 5,328,846, issued to Wedler on Jul. 12, 1994, teaches a method of removing mucin from a contact lens with a composition including a buffering agent, an alpha-amylase from *Bacillus licheniformis* (a mucin-degrading enzyme) and calcium ions. A preferred method involves finger rubbing of the contact lens.

U.S. Pat. No. 5,491,091, issued to Loshaek, et al. on Feb. 13, 1996, discloses a process of disinfecting contact lenses in peroxide solutions having a concentration of 0.01 to 0.5 weight/volume percent peroxide. The peroxide may be produced from a solid perborate which is in tablet form. The tablet may include a solid acid and a solid carbonate, which, when reacted in solution, generate a carbon dioxide effervescence for release of the perborate.

There remains a need for an apparatus and method of thoroughly mixing the composition of a contact lens cleaning and/or disinfection solution. In addition, while mechanical agitation means have been disclosed in the art, there remains a need for a self-contained mixing system which does not require external energy sources.

SUMMARY OF THE INVENTION

An object of the invention is to provide an improved contact lens cleaning and disinfection system.

Another object of the invention is to provide a system for thoroughly mixing the solution components within a contact lens treatment container without use of external power sources.

A further object of the invention is to provide a contact lens treatment system for use with effervescent tablets.

One embodiment of the invention is an apparatus for cleaning and/or disinfecting contact lenses. The treatment apparatus includes (a) a container for holding treatment fluid, having an open top end and a closed bottom end; (b) a closure adapted to removably mate with the container to provide a substantially liquid-impermeable seal; and (c) a tubular channel affixed either to the closure or the container, providing a pathway for fluid flow to enhance mixing. The tubular channel may extend downwardly from the closure towards the container bottom. Alternatively, the tubular channel may extend upwardly from the container bottom towards the closure. In either embodiment, the channel is open at both the end nearest the closure and the end nearest the container bottom, thereby providing a continuous pathway for fluid flow.

Another embodiment of the invention is an improved method of cleaning and/or disinfecting contact lenses. The method involves providing a lens treatment chamber and lens holding means therein and providing a means for mixing fluids in the treatment chamber which does not require external power supplies. In a preferred embodiment, the method involves providing an effervescent tablet in the bottom of the container and a tubular channel substantially centered over the tablet. The tablet generates gas (and, optionally, active agents) which rises upwardly through the channel, thereby inducing an upward flow of fluid through the channel. The force of gravity on fluid exiting the top of the channel causes a downward flow of fluid (and active agents, if present) between the outside of the channel and the interior walls of the container. These currents cause a continuous mixing of fluids within the container, thereby enhancing concentration uniformity throughout the container.

DESCRIPTION OF THE PREFERRED EMBODIMENTS

Figure 1:
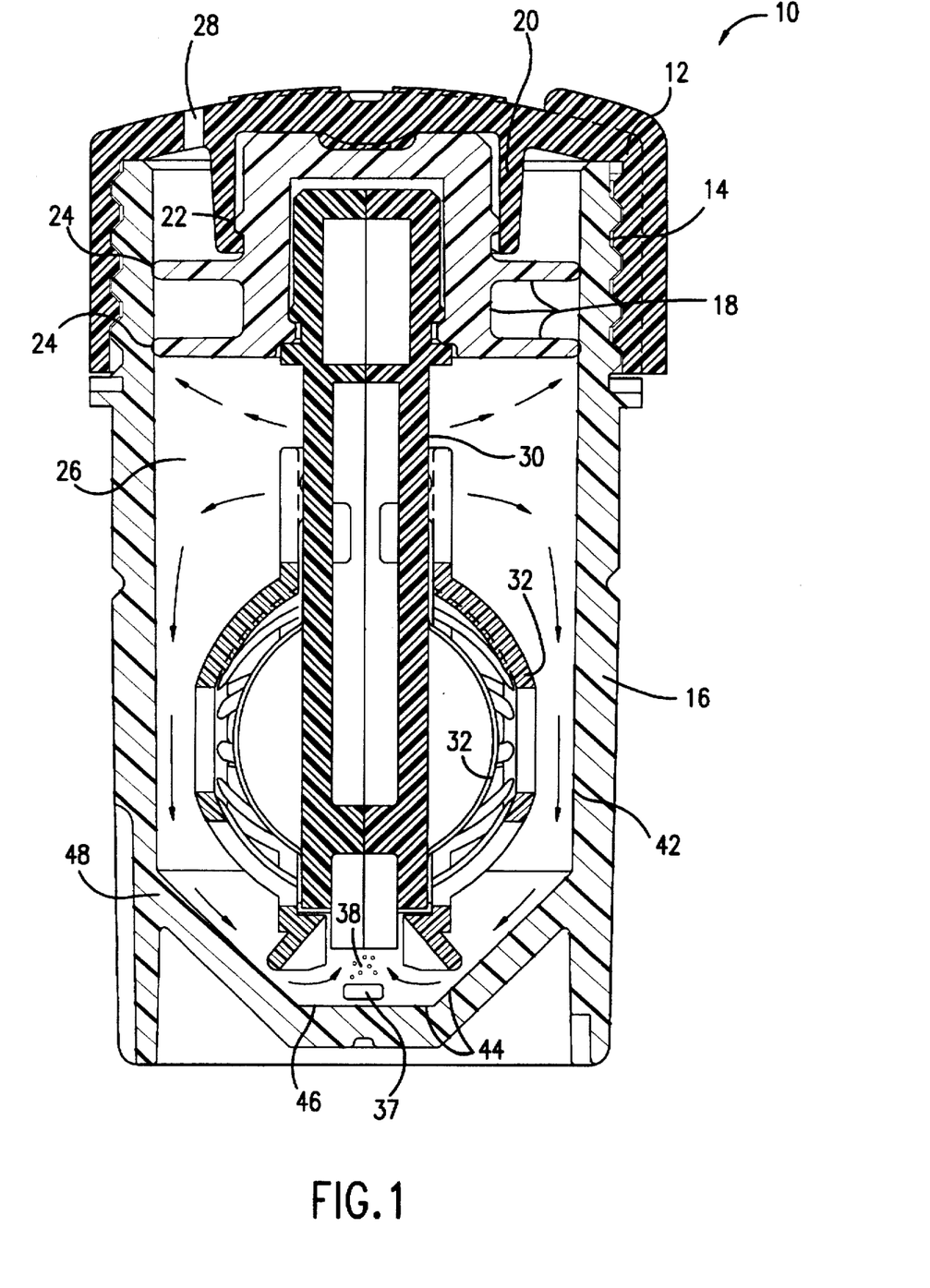
FIG. 1 is a side sectional view of a contact lens treatment system of the present invention.
Figure 2:
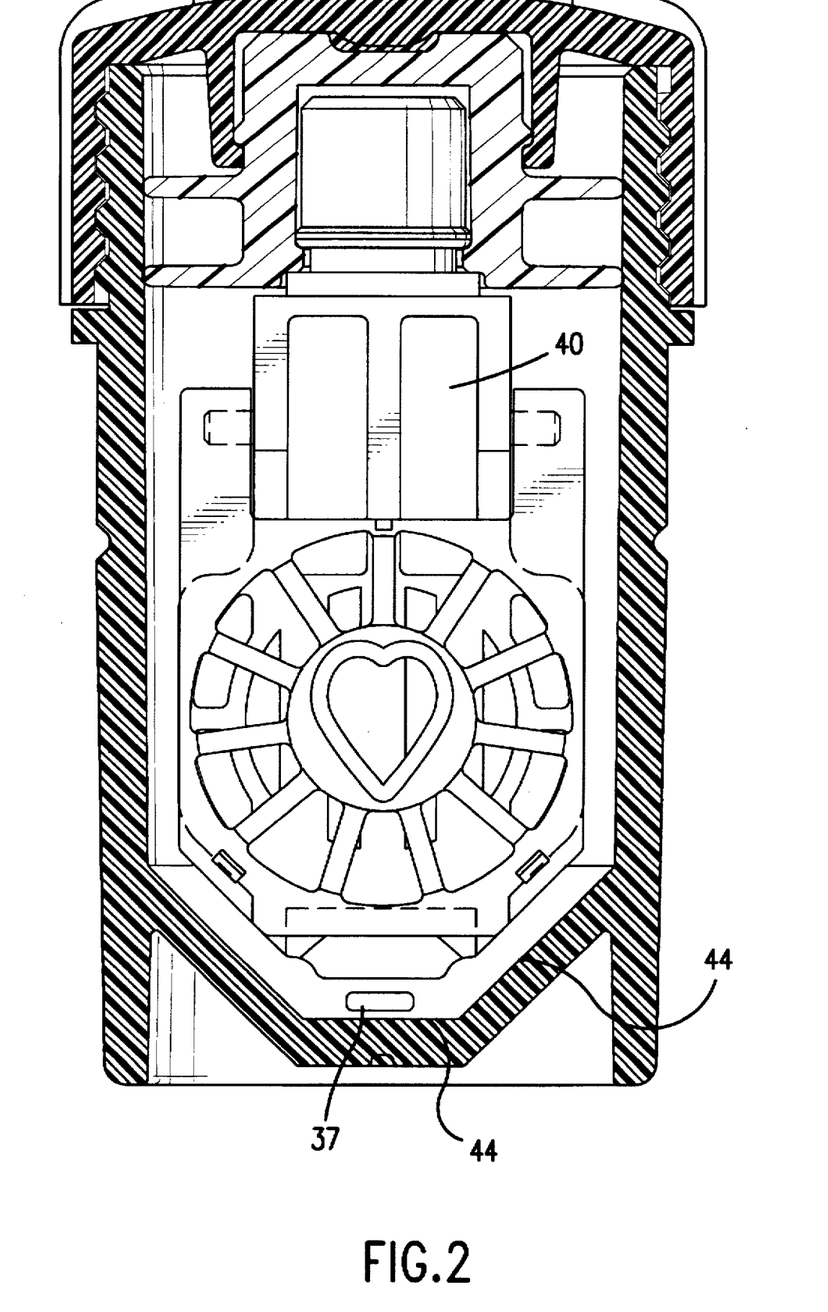
FIG. 2 is a side sectional view of the contact lens treatment system of FIG. 1 rotated 90°.

The invention may be best understood with reference to the drawings. FIGS. 1 and 2 are side sectional views of a contact lens treatment system 10 of the present invention. System 10 includes closure 12 which is releasably affixed, preferably via mating threading 14, to the top of container 16. The container is adapted to receive and hold ophthalmic lenses, especially contact lenses, and a volume of fluid sufficient to treat the lenses. Preferably, the container has a substantially circular top opening and a closed bottom. A preferred container shape is cylindrical. Preferred treatments are disinfection, cleaning, and both cleaning and disinfection. However, a variety of other treatments, such as lens lubrication or hydration, are within the scope of the invention.

Closure 12 has deformable sealing means 18 affixed thereto by an interference fit between the top side walls of sealing means 18 and cylindrical extension member 20 at location 22. When closure 12 is affixed to container 16, a substantially liquid-impermeable circular seal is formed between sealing means 18 and the interior walls of container 16 at two locations 24.

The sealing of closure 12 to container 16 defines treatment chamber 26. The deformable sealing means prevents liquid held within the treatment chamber from leaking out when the system is tilted or turned upside down.

Closure 12 also includes opening 28 extending through the closure to the ambient environment. In operation, when gas pressure reaches a certain level above ambient pressure, sealing means 18 deform and allow gas to vent past the sealing means and through opening 28. In some embodiments, the gas pressure may elevate during the lens treatment process, thereby causing venting to the environment. However, in other embodiments, venting only occurs, if at all, during quick assembly by the user, and not continuously during the treatment process.

The shape of opening 28 may vary widely (e.g., rectangular, oval, slits) and still be within the scope of the invention. In fact, while it is preferred to have an opening to the environment, the invention is not limited to containers which have openings. A preferred shape of opening 28, with respect to manufacturing efficiency, is a circular opening. While only one opening is shown in this embodiment, it is clearly within the scope of the present invention to have a plurality of openings extending through the closure.

Moreover, while the sealing and venting system illustrated in FIGS. 1 and 2 is a preferred system, numerous other sealing and venting systems may be used in accordance with the present invention. Examples of other sealing and venting systems include those disclosed in U.S. Pat. No. 4,011,941 (O-ring positioned in an annular groove passageway), issued to Parsons on Mar. 15, 1977 ; U.S. Pat. No. 4,637,919 (cap includes a filter assembly positioned in a vent passageway), issued to Ryder, et al., Jan. 20, 1987; U.S. Pat. No. 4,750,610 (gas vents around deflectable flange in cap and through loosely threaded container-cap connection), issued to Ryder, Jun. 14, 1988; U.S. Pat. No. 4,956,156 (cap having a bore with a post is positioned in the bore and a deflectable diaphragm positioned around the post), issued to Kanner, et al., Sep. 11, 1990; U.S. Pat. No. 4,996,027 (self-reseating unitary gasket is positioned between the cap and container), issued to Kanner, Feb. 26, 1991; and U.S. Pat. No. 5,250,266 (cap includes disc having a linear slit therethrough), issued to Kanner, Oct. 5, 1993; all of which are incorporated herein by reference.

Figure 3:
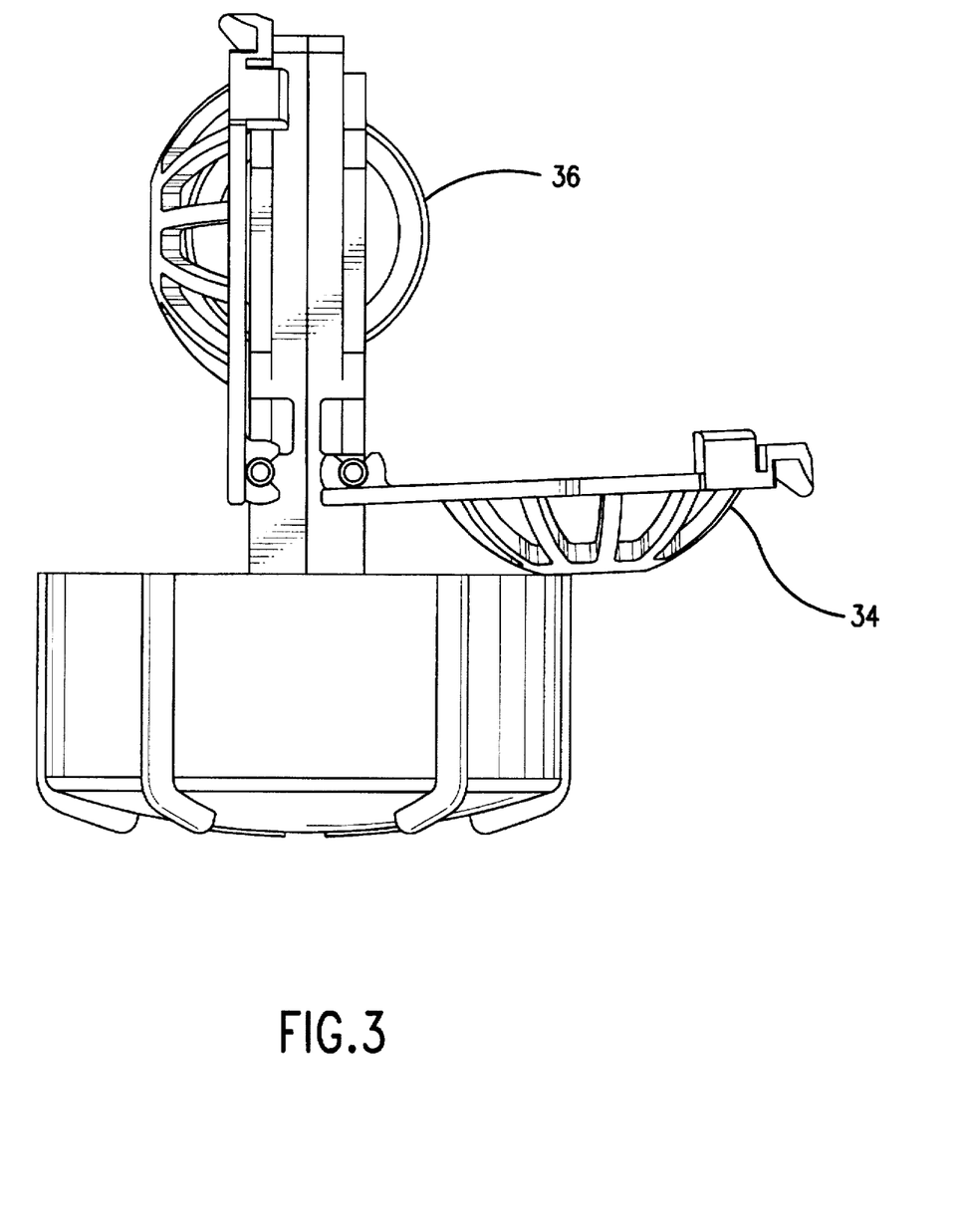
FIG. 3 is a side view of the closure and associated lens-retaining means of the systems of FIGS. 1 and 2.

As shown in FIGS. 1 and 2, elongated member 30 is affixed to sealing means 18, which, in turn, is affixed to closure 12. Elongated member 30 supports lens-retaining means 32, which includes basket 34 and a convex-shaped dome member 36 (shown in FIG. 3). Basket 34 may be opened, as shown in FIG. 3, when the closure and attachments are removed from the container. Lenses may be inserted into or removed from each of the lens retaining means when basket 34 has been pivoted into an open position.

Many alternative embodiments of the arrangement of the elongated member may be envisioned which are within the scope of the present invention. For example, the elongated member may alternatively be affixed directly to the closure, rather than being affixed to the sealing means. In another embodiment, the elongated member may be releasably affixed to the bottom of the container. In yet another embodiment, the elongated support member may be releasably affixed to the container side walls. However, the elongated member is preferably affixed to the closure, so that the consumer may remove the contact lens holding means at the same time as the closure is removed.

Figure 4:
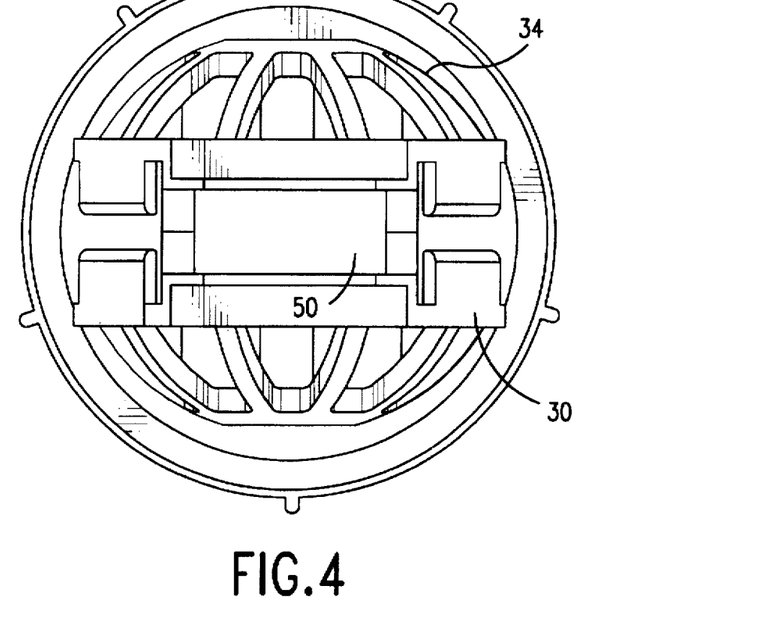
FIG. 4 is a bottom view of the lens holding assembly and channel of the FIG. 1 lens treatment system.

An especially important feature of the present invention is a fluid flow conduit or channel which facilitates fluid mixing and uniform concentrations within the treatment chamber. The term "channel", as used herein, refers to a means for guiding fluid flow, including tubular conduits or passageways, whether closed or open. FIG. 4, which is a bottom view of elongated support member 30 and lens-retaining means 32, illustrates channel 50 which extends upwardly through the center of elongated support member 30 towards the opening of the container. The channel may have a variety of shapes in cross section, including the more common square, oval, rectangular, and circular. There is no requirement that the channel have a uniform cross-sectional shape, but a uniform shape is believed to better promote flow due to reduced resistance relatively to non-uniform shapes. The rectangular cross sectional shape of channel 50 may be preferred from the perspective of manufacturing efficiency.

The dimensions of channel 50 may vary somewhat depending on the specific application. In general, the ideal length of the tubular channel is a function of the length of the container side walls. Preferably, the tubular channel extends a distance at least 50% of the length from the closure to the container closed bottom end. More preferably, the channel extends a distance of 75% of the length from the closure to the container closed bottom end. More preferably, the channel extends a distance of 90% of the length from the closure to the container closed bottom end. A preferred length of channel 50, extending from the bottom of the container to the top, is about 4 mm to about 50 mm. More preferably, the length of channel 50 is between about 8 mm and about 30 mm. The cross-sectional area of channel 50 through which fluid flows preferably is within about 1 $mm^2$ to about 100 $mm^2$, more preferably about 7 $mm^2$ to about 60 $mm^2$.

The channel is designed to promote fluid flow in a uniform direction, preferably upwardly towards channel opening 40 (See FIG. 2). In operation, fluid flow may be initiated when an effervescent tablet 37 begins generating gas (e.g., carbon dioxide), which rises through the fluid. The rising gas bubbles induce a flow of fluid, and optional active agents, upward through channel 50, as shown by the arrows near the bottom of the container in FIG. 1. Gas exit through openings 40 (see upward arrows). If sufficient internal pressure develops, gas may eventually escape through sealing means 18 near seal locations 24 by deflecting or deforming the sealing means. The gas which passes through the sealing means finally exits the system through opening 28.

Meanwhile, fluid which was induced to flow upwardly with the gas, also exits at openings 40 in channel 50. However, gravity causes the fluid, and optional suspended agents, which exits openings 40 to flow downward between elongated support member 30, through and between basket 34 and convex dome member 36, both in front of and behind the lenses. Fluid also flows downward between basket 34 and side walls 42 of the container (see downward arrows). This gas and fluid flow cycle continues as long as the effervescent tablet continues to generate gas.

Preferably, the effervescent tablet is located at the bottom of the container and substantially in the center. It is also preferable that the effervescent tablet be located nearly directly below channel 50, in order to promote the most uniform flow regime and the smallest concentration gradient. In order to achieve a relatively precise and accurate placement of the effervescent table as described, the system preferably includes a tablet alignment means.

FIGS. 1 and 2 illustrate a preferred tablet alignment means. The means for tablet alignment may be selected from a variety of shapes designed to cause the tablet to self-align when dropped into the container. A preferred tablet alignment means is shown in FIGS. 1 and 2. Tablet alignment means 44 is a funnel-shaped bottom of container 16, which has an apex located in the center of the container. The central area of the bottom of the container is preferably horizontal when the container is resting upright, in normal use conditions. Central area 46 of the tablet alignment means is preferably slight greater than the longest dimension of the effervescent tablet to be used. Preferably, central area 46 is circular and ranges from about 10 to about 200 mm², more preferably about 25 to about 100 mm², and even more preferably from about 35 to about 80 mm². The peripheral walls 48 of the alignment means are preferably angled at about 120° to about 150° upwardly from the horizontal central area, and extend to meet vertical side walls 42 of the container. When a tablet is dropped into the container by a consumer, gravity causes the tablet to impact the bottom of the container, and if the impact is on the peripheral angled walls, the tablet will slide down the walls, coming to a rest in the horizontal central area. Thus, tablet alignment means 44 functions to essentially automatically and uniformly align the tablet into the center of the container bottom.

In an alternative embodiment, the tablet may be inserted directly into the tubular channel. The tablet may be inserted into the bottom of the channel in the opening shown in FIG. 5. Alternatively, the tablet may be inserted from the top of the tubular channel. In yet another embodiment, an opening may be formed in one of the sides of the tubular channel for insertion of the tablet. In any embodiment in which the tablet is lodged in the tubular channel, it is preferred to include some means by which the tablet may be retained in position in the channel. For example, the baffles or protuberances shown in the FIG. 6 embodiment may perform this tablet retention function. One advantage of locating the tablet in the tubular channel is that no additional tablet alignment means in the bottom of the container is necessary.

Figure 5:
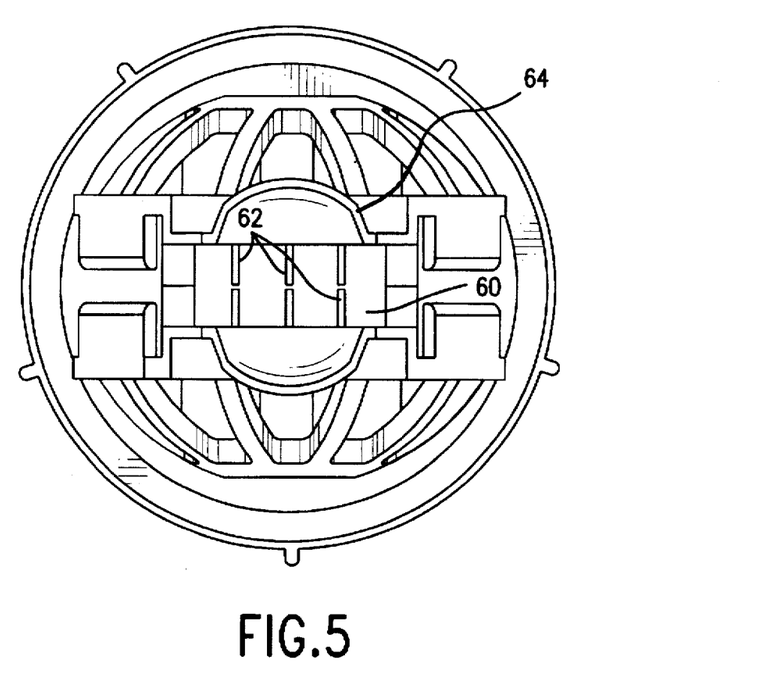
FIG. 5 is a bottom view of an alternative lens holding assembly and channel of another embodiment of the lens treatment system.

FIG. 5 shows another embodiment of the present invention, which illustrates two optional and advantageous features for promoting flow and fluid mixing. FIG. 5 is a bottom view of an alternative lens holding assembly and channel which includes a plurality of baffles 62 positioned throughout tubular channel 60. The baffles increase mixing in order to further reduce concentration gradients in the treatment fluid. Preferably, the baffles protrude from both internal faces of the channel walls about half of the width of the channel.

Figure 6:
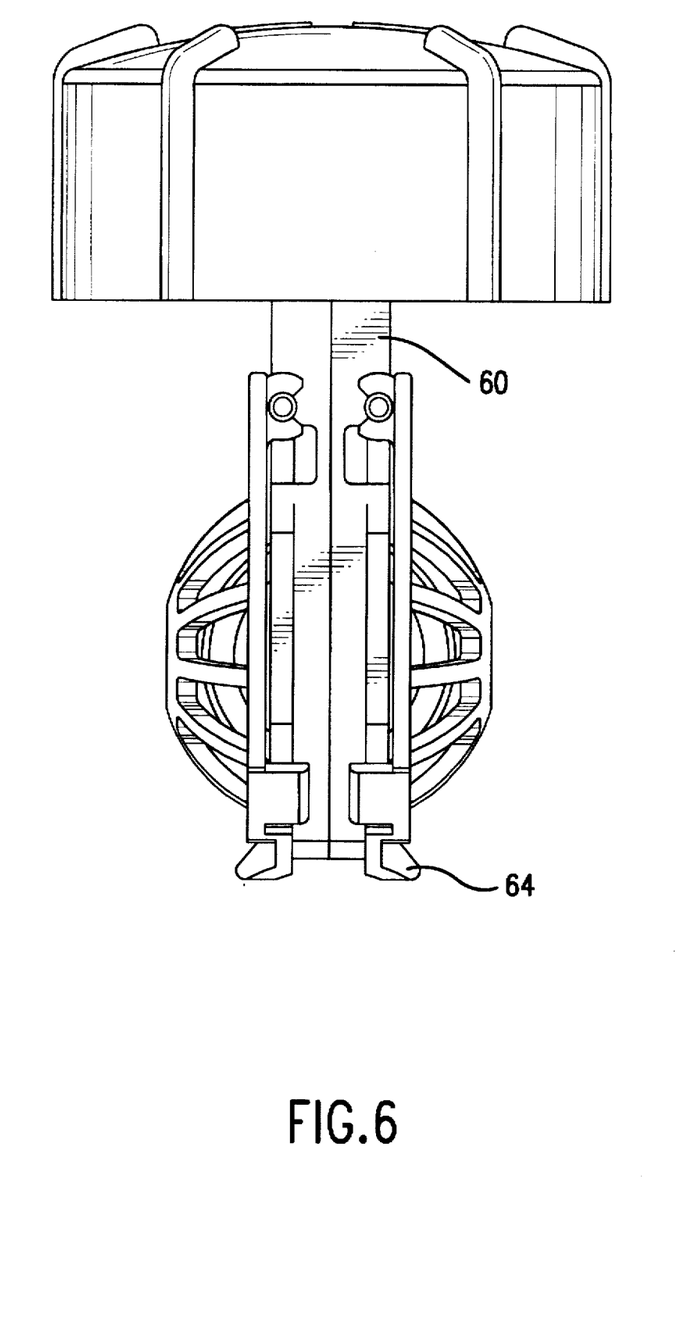
FIG. 6 is a side view of a flow guide member.

The FIG. 5 embodiment also includes a flow guide member 64 affixed to the bottom end of tubular channel 60. A side sectional view of the flow guide member is shown in FIG. 6. Flow guide member 64 is a conical or funnel shaped extension member which is formed when baskets 34 are closed over dome 36. Flow guide member 64 flares outwardly from the bottom of channel 60. The flow guide member provides a means for funneling the effervescent bubbles and fluid flow into the tubular channel, thereby reducing the likelihood of stagnation points or disruptive countercurrents. Thus, the flow guide member may also be added to improve concentration uniformity throughout the treatment container. In addition, flow guide member 64 aids in aligning the tablet in the center of the container bottom.

Preferably, the flow guide member extends a distance of about one millimeter to about 10 millimeters from the bottom edge of the tubular channel. The flow guide member is preferably concave in shape, having a radius of curvature of about 1to about 10 mm, more preferably about 3 to about 5 mm. The flow guide member preferably has an angle of about 30° to 60° with the tubular channel.

The components of the treatment system may be formed from a wide variety of materials. However, the sealing and venting means is formed from a resiliently flexible material so that the rims may be deformed by internal pressure to provide a vent passageway between the sealing means and the container wall for venting, if and when excessive internal pressure develops. Preferred materials include polypropylene, polyethylene and polyethylene terephthalate.

The disinfecting and/or cleaning components used with this system may be chosen from a wide variety of known disinfectants and cleaners. A class of lens treatments useful in accordance with the present treatment system is one in which one or more components must be separated from the other components of the treatment system prior to use.

For example, a peroxide solution disinfectant, such as the popular AOSept® 3% hydrogen peroxide solution, may be added to the container as the disinfectant. A tablet including an effervescent couple and a peroxide decomposition catalyst, such as catalase or some form of platinum, may be added to the peroxide solution. A delayed release coating may be applied to the tablet. In operation, the peroxide will disinfect lenses while the effervescent tablet releases decomposition catalyst over time, eventually decomposing substantially all of the peroxide into water and oxygen. Use of the present system provides good mixing and concentration uniformity, thereby reducing the time required for catalytic decomposition of the peroxide.

Another example of treatment compositions which are especially advantageously used with the present treatment system are those in which disinfecting or cleaning is initiated when all the components are combined, but the active period for disinfection or cleaning is a limited period. These treatment compositions must be shipped and stored in separate containers and mixed immediately prior to or during use. The present treatment system is especially advantageous when used with the compositions described in U.S. Pat. Nos. 4,473,550; 4,588,586; and 5,169,455; all of which are incorporated herein by reference.

For example, a tablet including horseradish peroxidase, potassium iodide and sodium perborate, in addition to an effervescent couple may be formed. A saline solution may be placed in the present lens treatment container along with the tablet. Contact lenses may be placed in the present lens-retaining means and the lenses-retaining means immersed into the saline solution in the container. As the tablet dissolves, the disinfection components release and travel primarily upward with the effervescent bubbles through the central tubular channel, then downwardly between the container walls and through the lens-retaining means, thereby bathing the lens on both convex and concave surfaces.

Thus, the invention is not limited to the composition of the treatment system. A variety of disinfection, cleaning, neutralizing, conditioning and storing solutions may be beneficially used with the instant treatment apparatus.

In another embodiment, the invention is directed to a method of mixing fluids in a container. The method involves the steps of (a) providing a container adapted to retain a volume of fluid, having an open top end and a closed bottom end; (b) providing a closure adapted to removably mate with said container to provide a seal which is substantially liquid-impermeable; (c) providing a tubular channel affixed to the closure, extending downwardly from the closure into the container towards said closed bottom end; and (d) providing an effervescent means at the closed bottom end of the container, thereby causing flow upward through the tubular channel and flow downward between the tubular channel and the container.

In a preferred embodiment, the invention is directed to a method of treating ophthalmic lenses, especially contact lenses. The method involves (a) providing a container adapted to retain a volume of fluid, having an open top end and a closed bottom end; (b) providing a closure adapted to removably mate with said container to provide a seal which is substantially liquid-impermeable, wherein the closure includes: (1) a support stem affixed to the closure and extending substantially perpendicularly from the closure into the container, (2) a tubular channel within the support stem, extending downwardly from an area near the closure into the container towards the closed bottom end, and (3) means for retaining lenses in the container, wherein the lens-retaining means is affixed to the stem; and (c) providing an effervescent means at the closed bottom end of the container, thereby causing flow upward through the tubular channel and flow downward between the tubular channel and the container and through the lens-retaining means. A particularly preferred method involves simultaneously cleaning and disinfecting contact lenses.

The previous disclosure will enable one having ordinary skill in the art to practice the invention. The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, or the like are provided to enhance the reader's comprehension of this document, and should not be read as limiting the scope of the present invention. Accordingly, the intellectual property rights to this invention are defined only by the following claims and reasonable extensions and equivalents thereof.

That which is claimed is:

1. A treatment system, comprising:
   (a) a container adapted to retain a volume of fluid, having an open top end and a closed bottom end;
   (b) a closure adapted to removably mate with said container to provide a seal which is substantially liquid-impermeable; and
   (c) a tubular channel affixed to said closure, extending downwardly from said closure into said container towards said closed bottom end, wherein the tubular channel has openings therethrough, located nearer the closure than the closed bottom end of the container, which allows fluid to pass from inside the tubular channel to outside the tubular channel.

2. A treatment system of claim 1, wherein the tubular channel extends a distance at least 50% of the length from the closure to the container closed bottom end.

3. A treatment system of claim 1, wherein the closed bottom end of said container is funnel-shaped such that a tablet released into said container will seat substantially at the center of the closed bottom.

4. A treatment system of claim 1, wherein said closure has an opening therethrough to enable gas to purge from the container.

5. A treatment system of claim 2, wherein said channel extends a distance of at least 75% of the length from said closure to said container closed bottom end.

6. A treatment system of claim 5, wherein said channel extends a distance of at least 90% of the length from said closure to said container closed bottom end.

7. A treatment system of claim 1, wherein said channel is substantially centered within the container and extends substantially parallel to the container walls.

8. A treatment system of claim 1, wherein the system includes a vent passageway extending through between the sealing means of the closure and the container.

9. A treatment system of claim 1, wherein the closure seals to the container via mating threads on the closure and the container.

10. A treatment system of claim 1, wherein the tubular channel is substantially cylindrical.

11. A treatment system of claim 1, further including a tablet alignment means located at the bottom of the container for aligning one or more tablets with the tubular channel.

12. A treatment system of claim 11, wherein the container includes substantially vertical side walls and the tablet alignment means comprises:
   (a) a substantially horizontal central area; and
   (b) peripheral side walls extending angularly from the central area to the substantially vertical side walls of the container.

13. A treatment system of claim 12, wherein the angled walls form an angle of 120° to 150° with the central area.

14. A treatment system of claim 12, wherein the horizontal central area has an area of about 10 to about 200 mm$^2$.

15. A treatment system of claim 1, wherein the length of the channel is about 4 mm to about 50 mm.

16. A treatment system of claim 1, wherein the cross-sectional area of the channel through which fluid flows is from about 1 mm$^2$ to about 100 mm$^2$.

17. A treatment system of claim 1, further including protuberances extending through said channel to promote fluid mixing.

18. A treatment system of claim 1, further including a flow guide member extending about 1 to 10 millimeters from the bottom of the channel.

19. A treatment system of claim 18, wherein said flow guide member has a concave surface facing the bottom of the container.

20. A treatment system of claim 1, further comprising means for retaining lenses affixed to the exterior walls of the tubular channel.

21. A treatment system, comprising:
  (a) a container adapted to retain a volume of fluid, having an open top end and a closed bottom end;
  (b) a closure adapted to removably mate with said container to provide a seal which is substantially liquid-impermeable; and
  (c) a tubular channel affixed to said container, extending upwardly from a point adjacent the bottom of said container to a point below said closure, said tubular channel having at least one opening at the top of the channel and at least one opening at the bottom of the channel.

22. A treatment system of claim 21, wherein the tubular channel extends a distance at least 50% of the length from the closure to the container closed bottom end.

23. A treatment system of claim 21, wherein said closure has an opening therethrough to enable gas to purge from the container.

24. A treatment system of claim 21, wherein said channel is substantially centered within the container and extends substantially parallel to the container walls.

25. A treatment system of claim 21, wherein the container includes substantially vertical side walls and a tablet alignment means which comprises:
  (a) a substantially horizontal central area; and
  (b) peripheral side walls extending angularly from the central area to the substantially vertical side walls of the container.

26. A method of mixing fluids in a container, comprising:
  (a) providing a container adapted to retain a volume of fluid, having an open top end and a closed bottom end;
  (b) providing a closure adapted to removably mate with said container to provide a seal which is substantially liquid-impermeable;
  (c) providing a tubular channel affixed to the closure, extending downwardly from the closure into the container towards said closed bottom end, wherein the tubular channel has openings therethrough, located nearer the closure than the closed bottom end of the container, which allows fluid to pass from inside the tubular channel to outside the tubular channel; and
  (d) providing an effervescent means at the closed bottom end of the container, thereby causing flow upward through the tubular channel and flow downward between the tubular channel and the container.

27. A method of treating contact lenses, comprising:
  (a) providing a container adapted to retain a volume of fluid, having an open top end and a closed bottom end;
  (b) providing a closure adapted to removably mate with said container to provide a seal which is substantially liquid-impermeable, wherein the closure includes:
    (1) a support stem affixed to the closure and extending substantially perpendicularly from the closure into the container,
    (2) a tubular channel within the support stem, extending downwardly from an area near the closure into the container towards the closed bottom end, wherein the tubular channel and support stem define at least one opening, located nearer the closure than the closed bottom end of the container, which allows fluid to pass from inside the tubular channel to outside the tubular channel, and
    (3) means for retaining lenses in the container, wherein the lens-retaining means is affixed to the stem; and
  (c) providing an effervescent means at the closed bottom end of the container, thereby causing flow upward through the tubular channel and flow downward between the tubular channel and the container and through the lens-retaining means.

28. A method of claim 27, wherein the lenses are simultaneously cleaned and disinfected.

* * * * *